(12) United States Patent
Most et al.

(10) Patent No.: US 10,298,225 B1
(45) Date of Patent: May 21, 2019

(54) ELECTRICAL SYSTEM FOR A PORTABLE ELECTRONIC DEVICE

(71) Applicants: Matthew Isaac Most, Boulder, CO (US); Trevor Glen Vita, Boulder, CO (US)

(72) Inventors: Matthew Isaac Most, Boulder, CO (US); Trevor Glen Vita, Boulder, CO (US)

( * ) Notice: Subject to any disclaimer, the term of this patent is extended or adjusted under 35 U.S.C. 154(b) by 837 days.

(21) Appl. No.: 14/959,976

(22) Filed: Dec. 4, 2015

Related U.S. Application Data (60) Provisional application No. 62/087,749, filed on Dec. 4, 2014, provisional application No. 62/087,751, filed on Dec. 4, 2014, provisional application No. 62/088,048, filed on Dec. 5, 2014, provisional application No. 62/087,747, filed on Dec. 4, 2014.

(51) Int. Cl.
| | |
|---|---|
| *B01F 1/00* | (2006.01) |
| *B23K 13/08* | (2006.01) |
| *H03K 17/56* | (2006.01) |
| *H05B 1/02* | (2006.01) |
| *A24F 47/00* | (2006.01) |

(52) U.S. Cl.
CPC .............. *H03K 17/56* (2013.01); *H05B 1/02* (2013.01); *A24F 47/008* (2013.01)

(58) Field of Classification Search
CPC ....... H03K 17/56; A24F 47/00; A24F 47/002; A24F 47/004; A24F 47/008; H05B 1/0202; H05B 1/0244; H05B 1/025

USPC .......................... 392/386–406; 219/482–509
See application file for complete search history.

(56) References Cited

U.S. PATENT DOCUMENTS

| | | | | |
|---|---|---|---|---|
| 5,144,962 | A * | 9/1992 | Counts | A24F 47/008 128/200.14 |
| 8,550,068 | B2 | 10/2013 | Terry et al. | |
| 2009/0230117 | A1 * | 9/2009 | Fernando | A24F 47/008 219/490 |
| 2011/0265806 | A1 * | 11/2011 | Alarcon | A24F 47/00 131/273 |
| 2013/0152922 | A1 | 6/2013 | Benassayag et al. | |
| 2014/0041655 | A1 | 2/2014 | Barron et al. | |
| 2014/0366894 | A1 * | 12/2014 | Liu | A24F 47/008 131/328 |
| 2015/0173124 | A1 | 6/2015 | Qiu | |
| 2016/0143359 | A1 * | 5/2016 | Xiang | H05B 1/0227 392/387 |

* cited by examiner

*Primary Examiner* — Sang Y Paik
(74) *Attorney, Agent, or Firm* — Marsh Fischmann & Breyfogle LLP; Russell T. Manning (57) ABSTRACT

The present disclosure is directed to an electrical system topology designed for use in a portable electronic device. The electrical system uses a conductive housing of the device to form a single main electrical circuit, which consists of forward microelectronics, rearward microelectronics and a battery. Through synchronized main circuit current modulation by the forward and rearward microelectronics, bidirectional communication is established between the forward and rearward sections of the device. The design allows for mechanical simplicity, which aids in product size reduction, increases mechanical robustness, reduces costs and enhances mechanical design flexibility.

17 Claims, 7 Drawing Sheets

ELECTRICAL SYSTEM FOR A PORTABLE ELECTRONIC DEVICE

CROSS-REFERENCE

The current application claims the benefit of the filing date of U.S. Provisional Application No. 62/087,747 having a filing date of Dec. 4, 2014, the entire contents of which is incorporated herein by reference.

FIELD

The present disclosure relates generally to portable electronic devices. More specifically, the present disclosure relates to an electrical system topology for portable electronic devices.

BACKGROUND

Embedded microelectronics are computerized control and/or sensor systems having dedicated functions within a larger mechanical or electrical system. These systems are embedded as part of a complete device often including hardware and mechanical parts. Embedded systems control many devices in common use today. Some estimates indicate that up to 98 percent of all microprocessors are used in embedded systems.

Modern embedded systems are most commonly based on microcontrollers (i.e. CPUs with integrated memory or peripheral interfaces). The microcontrollers/processors used may be types ranging from general purpose to those specialized for specific computations, or even custom designed for the application at hand. Embedded microelectronics typically have limited processing resources, which can make them difficult to interface with and/or program. Nonetheless, due to the rapid pace of size and cost reduction, the use embedded microelectronics for control functionality continues to increase.

One specific area where embedded microelectronics are finding increased use is in portable electronic devices. Such portable electronic devices may incorporate more than one embedded controller to control different functions of the device. In a portable device incorporating two or more embedded controllers, it is often necessary to provide complex wiring to power the embedded controllers and allow the controllers to communicate if the operation of the two or more controllers is interrelated.

SUMMARY

The constant pressure for miniaturization in portable electronics imposes unique challenges for hardware designers and the present inventors have recognized that, in some instances, it may be advantageous to trade electronic complexity for mechanical simplicity. Along these lines, the presented disclosure is directed to a novel electrical system topology which leverages microelectronics to reduce mechanical complexity, enhance physical ruggedness, and allow for high mechanical design flexibility in compact portable electronic devices.

In one arrangement, the novel electrical system topology is utilized in a portable herb vaporizer. However, identical system design can be applied to a battery-operated flashlight, laser pointer, or similar device which contains a battery, an electrical load and a conductive housing. In any arrangement, the novel electrical system topology uses a two conductor connection (e.g., conductive housing of a device as a first electrical conductor, battery connections as a second electrical conductor) for both power and signal transfer between two active regions of a device. For example, separate microelectronic controllers may be powered by a common power source and may be in signal communication without the use of dedicated electrical wiring for such signal communication. Use of the conductive housing of the device for such functionality not only eliminates the need for dedicated electrical wiring but can also allow for rotary connections between device segments and/or permit easy battery replacement.

The electrical system topology includes separate microelectronics in the front and rear sections of a portable electronic device. At a basic level, the electrical system is comprised of a single main electrical circuit (e.g., loop), which is formed by the rearward microelectronics, the battery, the forward microelectronics and the conductive device housing. In such an arrangement, the rearward microelectronics and forward microelectronics are disposed in series in the main electrical circuit. In one embodiment, an electrical load is incorporated with the forward microelectronics. In one specific embodiment the load is a resistive heater which is located in the front section of the device and which is controlled by the forward microelectronics. The specific electrical load is not a constraining factor in the design, and could easily be replaced with anything relevant to the device form-factor such as a light bulb or laser diode.

In one arrangement, the forward and rearward microelectronics work together in synchronization to provide low impedance voltage from the battery to an electrical load in a forward section of the portable device. When power supply interruptions to the load can be tolerated, battery charging may be performed through a rear-mounted external power connection. Additionally, information can be transferred between the forward and rearward sections of the device through a switching protocol, which modulates current in the main circuit to encode and transfer information bi-directionally between the front and rear sections. In the herb vaporizer embodiment, this allows for implementation of a rear-mounted temperature dial, which controls the behavior of the forward microelectronics despite being electrically connected to the forward section by only the battery and conductive housing.

In one arrangement, the forward and rearward microelectronics are configured to alternately connect and disconnect from the main electrical circuit. In this regard, each of the forward and rearward microelectronics may include a switch (e.g., transistor) that allows for either directing power and current from the battery through the microelectronics (active mode) or bypassing the power and current from the battery around the microelectronics (passive mode). While in passive mode, the microelectronics may operate on power stored during a time while the microelectronics were in an active mode. For instance, a capacitor or bank of capacitors may be charged during active mode operation and these capacitors may discharge during passive mode to power the passive electronics. Most commonly, the forward and rearward microelectronics work in synchrony to alternate passive and active modes. That is, except for switching delays, one of the forward and rearward microelectronics is in active mode while the other is in passive mode. These modes may be reversed periodically or by request. In the latter regard, the microelectronics in passive mode may request changing modes upon its stored power falling below a predetermined amount.

The switches that allow the microelectronics to connect and disconnect from the main circuit may also be utilized to modulate current flow in the main circuit. For example, the forward or rearward microelectronics may toggle their respective switch to encode data in accordance with any acceptable protocol for receipt by the other microelectronics. Accordingly, each set of microelectronics may monitor the current flow to receive encoded data from the other set of microelectronics.

DETAILED DESCRIPTION

Reference will now be made to the accompanying drawings, which at least assist in illustrating the various pertinent features of the presented inventions. The following description is presented for purposes of illustration and description and is not intended to limit the inventions to the forms disclosed herein. Consequently, variations and modifications commensurate with the following teachings, and skill and knowledge of the relevant art, are within the scope of the presented inventions. The embodiments described herein are further intended to explain the best modes known of practicing the inventions and to enable others skilled in the art to utilize the inventions in such, or other embodiments and with various modifications required by the particular application(s) or use(s) of the presented inventions.

The present disclosure is directed to an electrical system topology which leverages microelectronics to reduce mechanical complexity, enhance physical ruggedness, and allow for high mechanical design flexibility in compact portable electronic devices. In the present disclosure, the electrical system topology is utilized in a portable herb vaporizer. However, identical system design can be applied to a battery-operated flashlight, laser pointer, or similar device which contains a battery, an electrical load and a conductive housing and the present disclosure is not limited to use with a portable vaporizer. In any arrangement, the novel electrical system topology uses a conductive housing of a device as an electrical conductor for both power and signal transfer. In the latter regard, two embedded microelectronic controllers may be powered and in signal communication without the use of dedicated electrical wiring for signal communication. For purposes of the present disclosure, a portable electronic device is initially discussed followed by a discussion of the electrical system topology as applied to the portable electronic device.

Portable Electronic Device

Figure 1A:
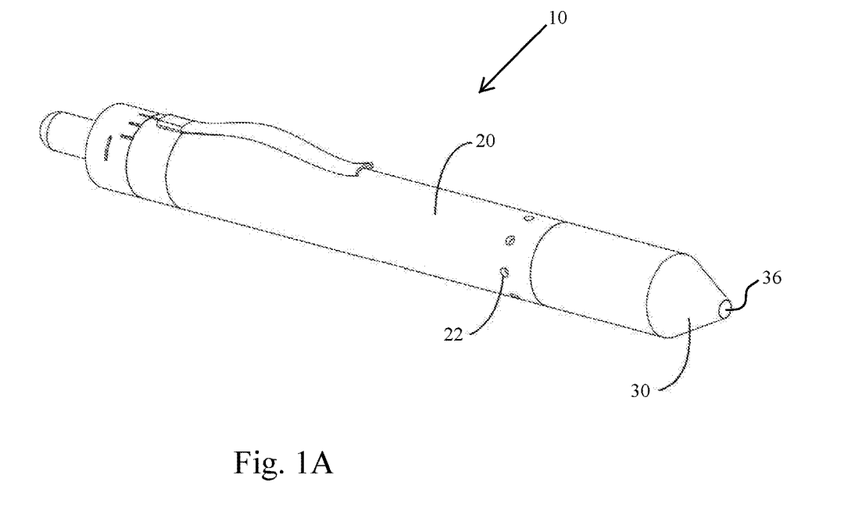
FIG. 1A is a perspective view of one embodiment of a vaporizer.

FIG. 1A illustrates a perspective of a portable vaporizer 10 for extracting active ingredients of herbs for inhalation. The vaporizer 10 is similar in size and form to a fountain pen. As shown, the vaporizer 10 includes a cylindrical body 20 and a mouthpiece 30. The mouthpiece 30 tapers to an opening 36 that a user utilizes to draw air into the vaporizer via air inlet apertures 22 in the cylindrical body 10. More specifically, the air is drawn through the interior of the vaporizer 10 where it passes through an internal heating element/heating exchanger, which heats the air to a desired temperature. The heated air passes through an internal herb chamber which holds a supply of herbs, which may be at least partially vaporized. The user draws the resulting vapor through the opening 36 in the mouthpiece.

Figure 1B:
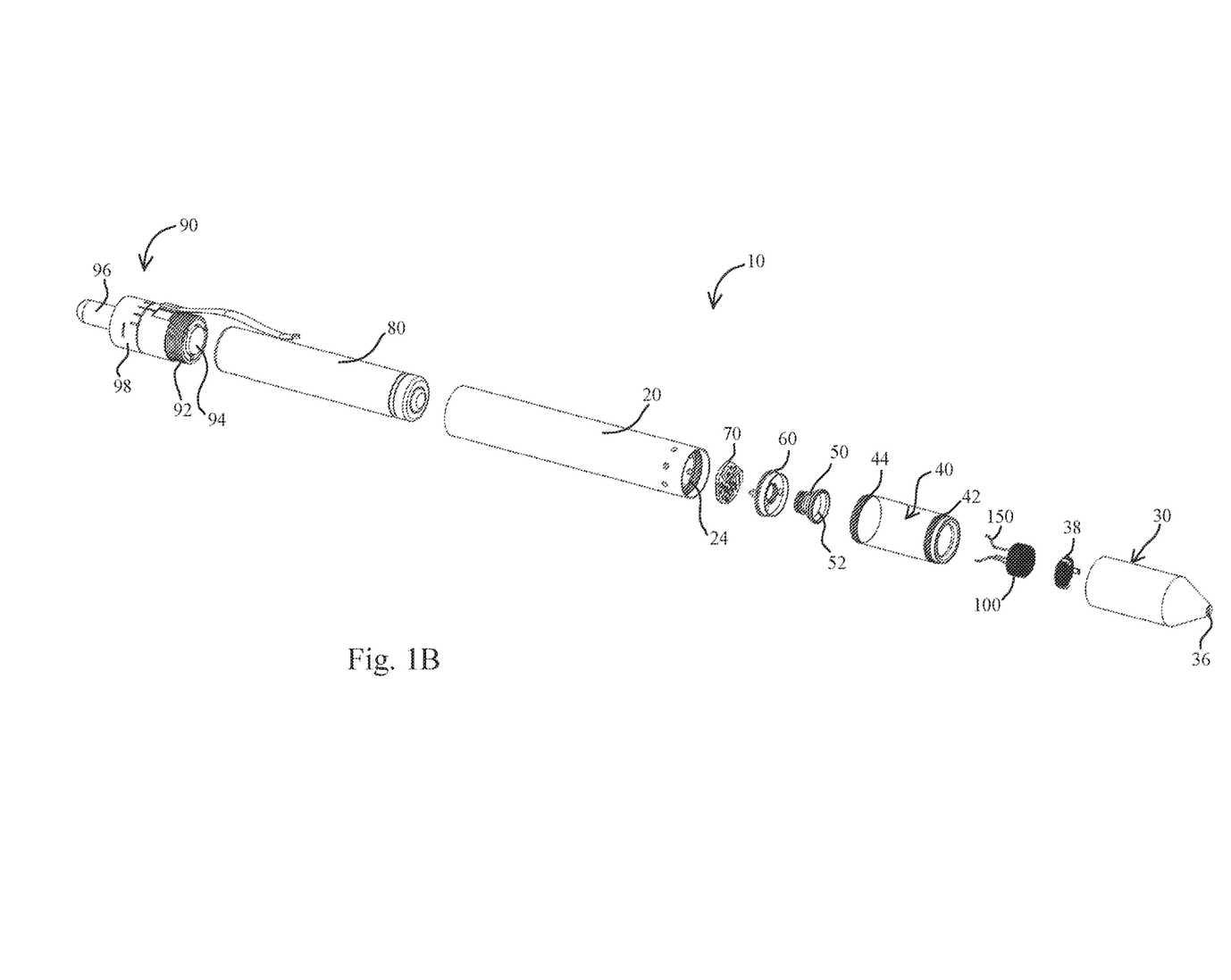
FIG. 1B is an exploded perspective view of the vaporizer of FIG. 1A.
Figure 1C:
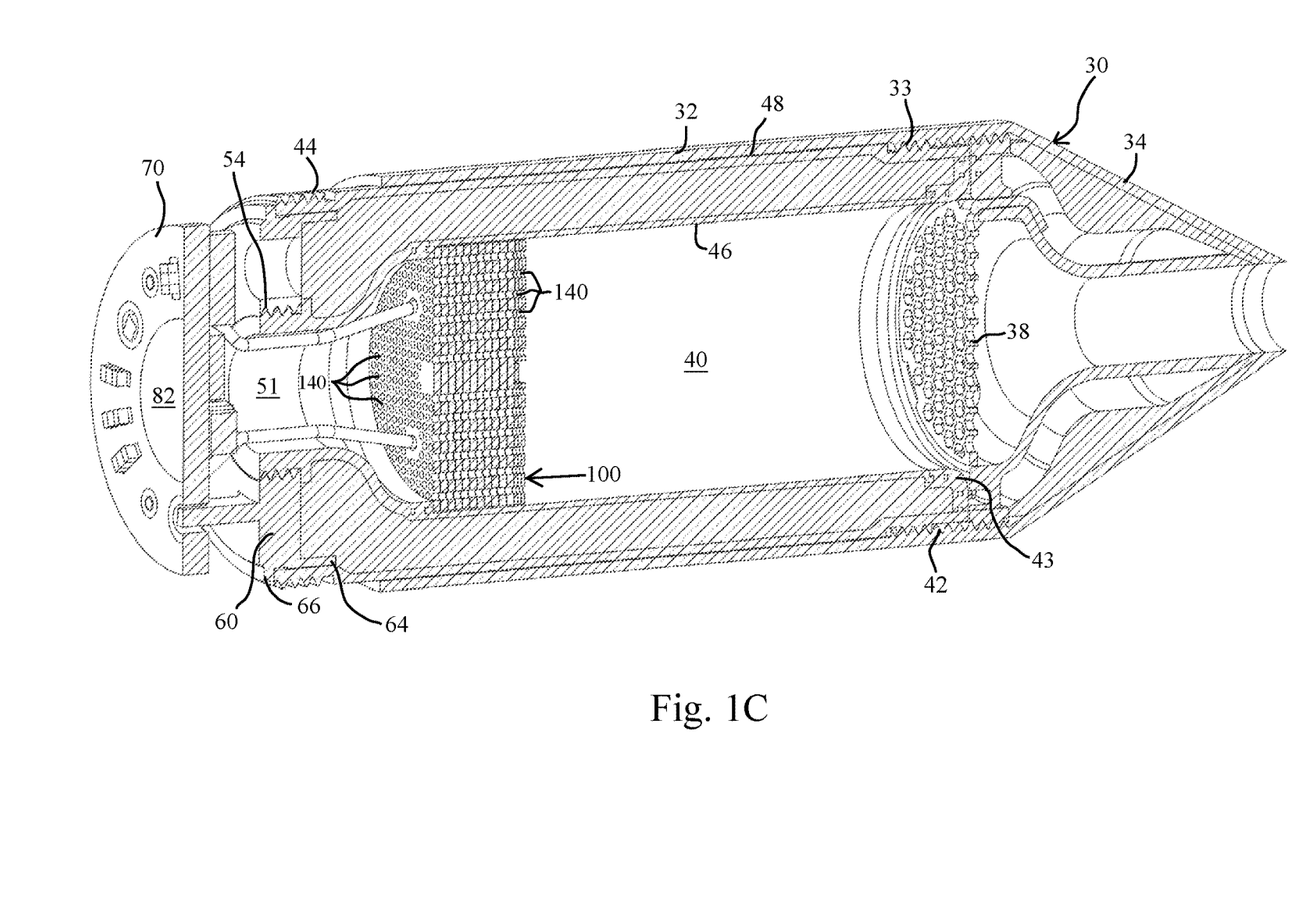
FIG. 1C is cross-sectional perspective view of a forward portion of the vaporizer of FIG. 1A.

FIG. 1B illustrates an exploded perspective view of the vaporizer 10 and FIG. 1C illustrates a cross-sectional view of an assembled forward portion of the vaporizer 10. As shown, the mouthpiece 30 is formed of a generally hollow cylindrical section 32 attached to a conical end section 34. The mouthpiece 30 includes internal threads 33 located near the transition between the cylindrical section 32 and the conical end section 34 as best shown in FIG. 1C. These internal threads 33 engage external threads 42 located on the forward end of a generally hollow herb chamber 40. External threads 44 on a rearward end of the herb chamber attach to internal threads 24 on a forward end of the cylindrical body 20. See FIG. 1B. In the present embodiment, when the mouthpiece 30 is in threaded engagement with the herb chamber 40, the cylindrical section 32 of the mouthpiece 30 extends over the herb chamber 40 and abuts with the forward end of the cylindrical body 10. See FIG. 1A.

Referring again to FIGS. 1B and 1C, a rearward interior portion of the herb chamber 40 houses a heating element 100, when the vaporizer 10 is assembled. A forward portion of the herb chamber 40 (i.e., in front of the heating element) provides an open internal space for placement of herbs. The heating element 100 is a convective heating element which heats air drawn into the herb chamber 40 from the air inlet apertures 22 in the cylindrical body. As illustrated, a screen 38 may be disposed within the mouthpiece 30 to prevent any particulate from passing through the device. In a further embodiment another screen (not shown) may be disposed within the herb chamber 40 proximate to the heating element 100.

An air nozzle 50 is positioned against a rearward end of the heating element 100 as best shown in FIG. 1C. The nozzle 50 extends from a small inlet aperture 51 (See FIG. 1C) to a larger exit aperture 52 (see FIG. 1B), juxtaposed against the rearward end of the heating element 100 to fluidly connect the inlet apertures 22 to the heating element 100, when the herb chamber 40 is in threaded connection with the cylindrical body 20. In the present embodiment, external threads 54 on a rearward end of the air nozzle 52 connect with internal threads of a mount 60 having a flange 64 received within the rearward end of the herb chamber 40. When assembled, the herb chamber 40 compresses a rim 66 of the mount 60 against the bottom of the internal threads 24 of the forward end of the cylindrical body 10. A rearward surface of the mount 60 supports a forward control circuit or forward circuit board 70. Connecting wires 150 (e.g., power wires, sensor wires etc.) of the heating element 100 pass through the air nozzle 50 for connection with the forward circuit board 70, which controls the operation of the heating element 100.

The cylindrical body 20 houses a battery 80 in its rearward portion behind the air inlet apertures 22. See FIG. 1B.

An end cap assembly 90 having external threads 92 engages internal threads (not shown) on a rearward portion of the cylindrical body 20. When the end cap assembly 90 is in threaded engagement with the cylindrical body 20, a forward terminal of the battery 80 engages a first electrical contact 82 of the forward circuit board 70 and a second contact 94 of the end cap assembly 90 engages a rearward terminal of the battery 80. The end cap assembly 90 includes a power button 96 that allows for activating and deactivating the device 10 (i.e., completing an electrical circuit). Additionally, the end cap assembly 90 further includes a temperature adjustment dial 98, which allows for adjusting the temperature of air passing through the device. The end cap assembly 90 further includes a rearward circuit board 76 which cooperates with the forward circuit board 70 to control the operation of the vaporizer 10. See FIG. 1D.

In use, a user removes the mouthpiece 30 from the herb chamber 40. Herbs are then placed within the forward portion of the herb chamber 40 in front of the heating element 100. At this time, a user may select a temperature setting using the temperature adjustment dial 98 and press the power button 96. The control circuitry then supplies electrical power to the heating element 100. Once the heating element achieves a desired temperature an indicator light (not shown) is illuminated to indicate that the vaporizer is ready for use. At this time, the user may draw air through the opening 36 in the mouthpiece, which draws air through the inlet apertures 22, through the nozzle 50, through the heating element 100 and through herbs within the herb chamber 40. The user receives vapors through the opening 36.

Electrical System Topology

Figure 1D:
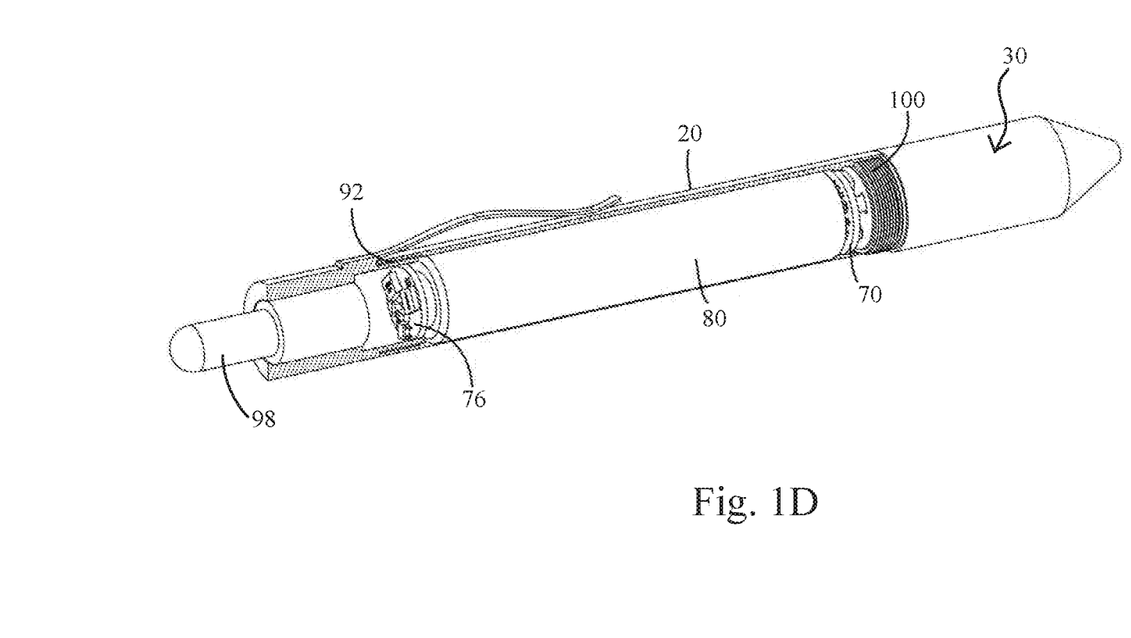
FIG. 1D is cross-sectional perspective view of a rearward portion of the vaporizer of FIG. 1A.

As noted, aspects of the presented inventions are directed to an electrical system for a portable device, which utilizes a device housing as an electrical conductor. FIG. 1D shows a perspective cutaway view of the vaporizer device 10 which incorporates the electrical system described herein. The conductive housing 20 forms an electrical connection from the forward control circuit/microelectronics 70 to the rearward control circuit/microelectronics 76. The battery 80 forms the second connection, which completes the main circuit. In the specific embodiment, threaded connections 24 and 92 allow for disassembly of the device 10 and replacement of the battery 80.

Figure 2A:
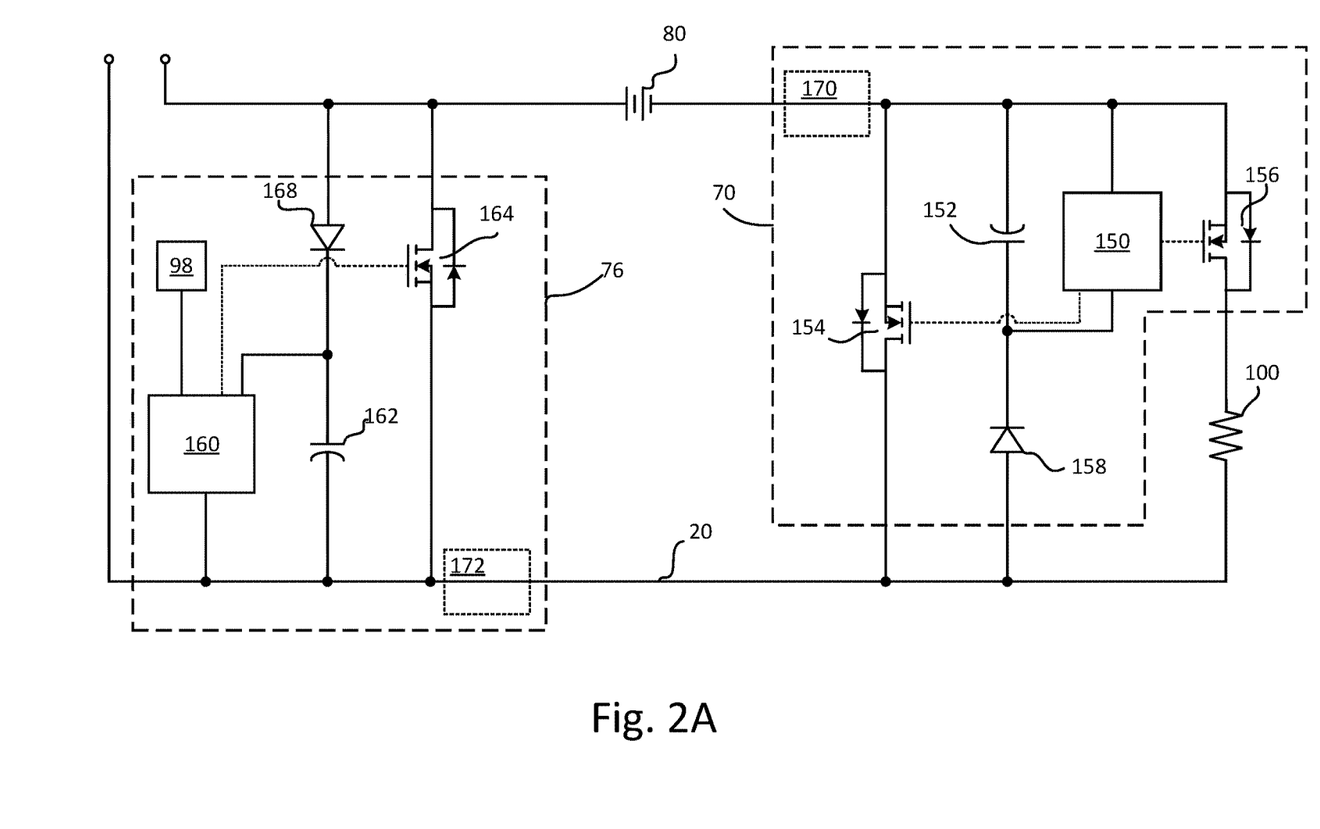
FIG. 2A is an electrical system topology.

FIG. 2A shows a simplified version of the electrical system schematic (e.g., electrical system topology). As shown, the forward control circuit 70 is connected in series with the rearward control circuit 76 via the battery 80 and the conductive housing 20. In this regard, the electrical system topology includes two isolated active electronics regions that are connected by only two connectors, which are used to share power and data. In the illustrated embodiment, the forward control circuit includes a forward microcontroller 150, a forward capacitor bank 152, a forward main transistor 154, a forward secondary transistor 156 and a forward diode 158. The forward control circuit 70 is electrically connected to a load, which is the resistive heating element 100 in the present embodiment. The rearward control circuit 76 includes a rearward microcontroller 160, a rearward capacitor bank 162, a rearward main transistor 164 and a rearward diode 168. The rearward control circuit is electronically connected to the temperature adjustment dial 98, which allows a user to adjust the temperature setting of the resistive heating element 100 in the present embodiment. The forward and rearward microcontrollers 150, 160 are integrated circuits containing a processor core, memory, and programmable input/output peripherals. Various pins of each microcontroller are connected to the main circuit, the transistor(s) and/or input devices (e.g., temperature adjustment dial). In the present embodiment, Amtel ATTiny 13A microcontrollers are utilized. These microcontrollers are 8-bit AVR RISC-based microcontrollers including 1 KB of ISP Flash, 64-byte EEPROM, 64-byte SRAM, 32-Byte register file, and 4-channel 10-bit A/D converter. However, it will be appreciated that any appropriate microcontroller may be utilized. Additionally, the forward control circuit and rearward control circuit may each further include current sensing electronics 170, 172, respectively, as is further discussed herein.

As shown, gates of forward and rearward main transistors 154, 164 (e.g., field-effect transistors) are controlled by the forward and rearward microcontrollers 150, 160 respectively. The microcontrollers 150, 160 work in a synchronized fashion to operate the transistors to provide power to the load 100 as well as replenish power to the capacitor banks 152, 162 as needed. That is, the microcontrollers 150, 160 are configured to open and close the transistors 154, 164 to power and isolate different regions of the electrical system topology. For instance, the forward active electronics region (e.g., forward control circuit 70) may be connected to the power source 80 while the rearward active electronics region (e.g., rearward control circuit 76) is isolated from the power source and operates using power from a temporary power source such as capacitor bank 162. That is, in a first mode of operation, the rearward main transistor 164 is closed/conducting (e.g., effectively a short between terminals 165a and 165b) and the forward main transistor 154 is open/non-conducting. See for example FIG. 2B. This causes voltage from the battery 80 to develop across the terminals 155a, 155b of the open forward main transistor. This low impedance voltage is available to power the forward microcontroller 150 and the load 100. In the present embodiment, the forward microcontroller 150 controls an optional forward secondary transistor 156 to controllably apply voltage to the load 100. In this first mode of operation, voltage from the battery 80 to the rear microcontroller 160 is interrupted. During such interruption, the rear microcontroller 160 is powered by the rear capacitor bank 162. Stated otherwise, during interruption, the rearward electronics region operates in a passive mode while the forward electronics region operates in an active mode.

The microcontrollers are operative to periodically or upon demand reconfigure the transistors 154, 164 to connect the rearward active electronics region to the power source 80 and recharge the capacitor bank 162. During such a reconfiguration the forward electronics region operates in a passive mode and is powered by the forward capacitor bank 152. That is, the state of the main transistors 154, 164 must be reversed to a second mode of operation (see FIG. 2C) periodically to replenish the capacitor bank 162 located in the rearward electronics region. During the second mode of operation, the forward capacitor bank 152 provides uninterrupted power to the forward microcontroller 150 and associated electronics. Forward and rearward diodes 158 and 168, respectively, prevent the capacitor banks 152 and 162 from discharging through transistors 154 and 164 when each is in the conducting state. Additionally, when the rearward transistor 164 is not conducting and forward transistor 154 is conducting, battery charging can be accomplished by means of an external power supply connected to terminals 175a, 175b. See FIG. 2C.

Figure 2B:
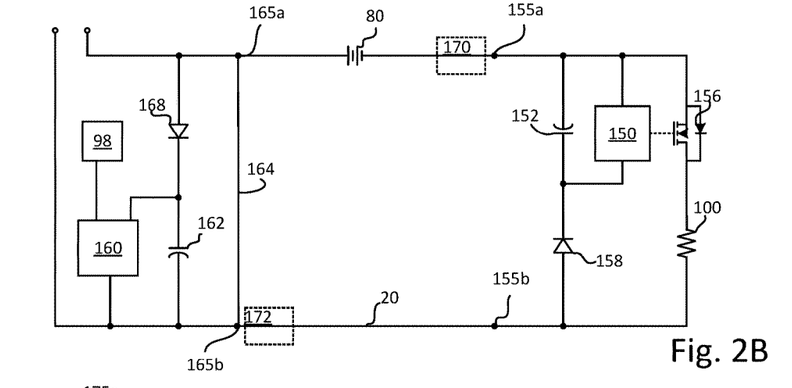
FIG. 2B is the electrical system topology in a first mode of operation where a rearward control circuit is isolated from a main circuit and a forward control circuit is powered by the main circuit.
Figure 2C:
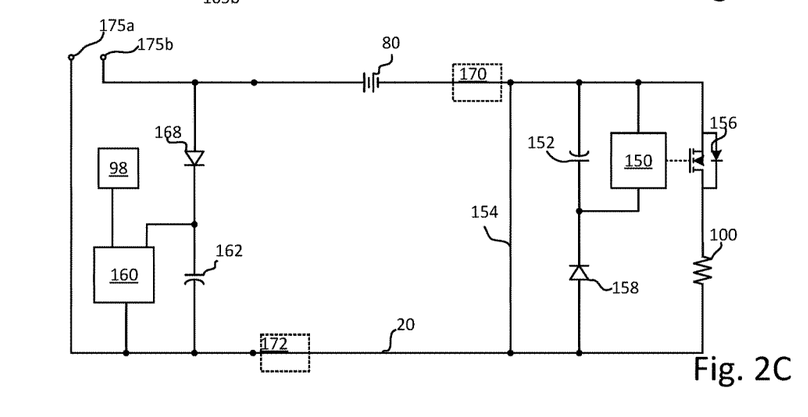
FIG. 2C is the electrical system topology in a second mode of operation where a forward control circuit is isolated from a main circuit and the rearward control circuit is powered by the main circuit.

The electrical system topology of FIGS. 2A-2C permits selectively isolating (i.e., by-passing) and powering two active electronics regions connected in a series loop by first and second conductors. More specifically, the forward and rearward control circuits 70, 76 are operative to connect to and disconnect from the main circuit loop utilizing the forward and rearward main transistors 154, 164, respectively, to open and close control circuit bypasses. That is, when the forward or rearward control circuit 70 or 76 closes its transistor 154 or 164, power from the main circuit loop bypasses the control circuit, the control circuit is isolated from the main circuit, and the control circuit operates on its capacitor bank. In contrast, when the forward or rearward control circuit 70 or 76 opens their respective transistor 154 or 164, the control circuit is powered by the main circuit.

The electrical system topology can also be utilized to transfer data between the forward and rearward control circuits or regions. To effect such data transfer, the forward and rearward control circuits may each include current sensing electronics 170, 172, respectively. These current sensing electronics can include a hall-effect current sensor, a shunt resistor with or without an op-amp for signal amplification, a comparator and voltage reference, or any other practical means of analog or digital current sensing. In any embodiment, current information is provided from the current sensing electronics to its respective microcontroller via an analog or digital interface. The current sensing electronics allow each active electronics region to monitor current flow and modulations of the current flow initiated by the other active electronics region. Such modulations may be in the form of a communication protocol.

By way of example, when the rearward main transistor 164 is conducting (See, e.g., FIGS. 2A and 2B) fluctuations in current draw by the forward electronics region can be detected by the rearward microcontroller 160. Further, current in the main loop can be modulated by the forward microcontroller 150 through switching of the main load 100 or switching of an auxiliary load. In this regard, information is transferred from the forward microcontroller 150 to the rearward microcontroller 160 through current modulation by the forward microcontroller 150 and subsequent detection of that modulation by the rearward microcontroller 160.

Information can also be transferred from the rearward active region to the forward active region of the device by similar means. If the forward microcontroller 150 is passing current to the load 100 (e.g., FIGS. 2A and 2B), toggling the rear main transistor 164 will modulate this current. Accordingly, the forward current-sensing circuitry 170 can detect this modulation, which provides a means of communication from the rearward microcontroller 160 to the forward microcontroller 150. If the main load 100 is of sufficiently low impedance, the forward current-sensing circuitry 170 can be omitted and the load itself can be used as the current shunt.

Figure 3A:
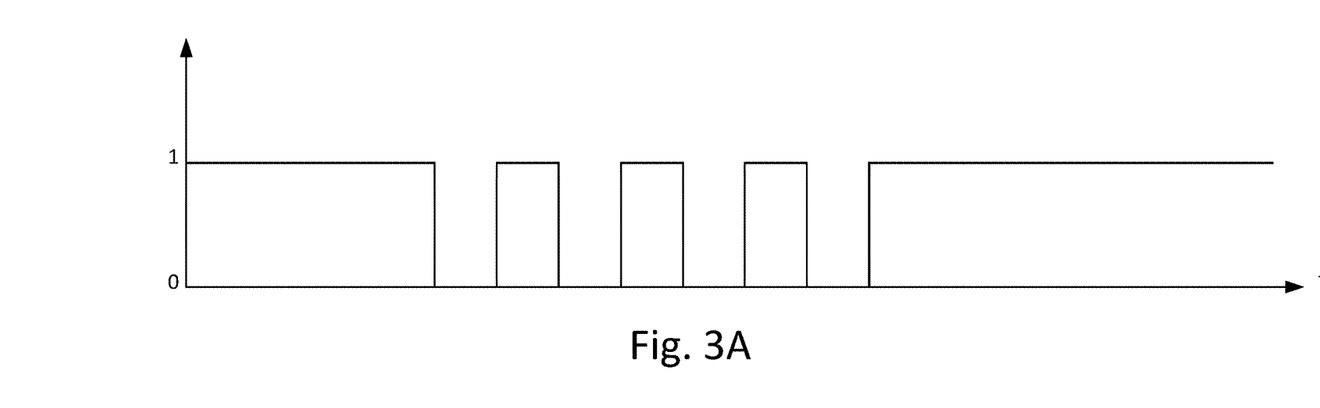
FIGS. 3A and 3B illustrate modulation of the main control circuit.

FIG. 3A illustrates one embodiment of a current in the main circuit as monitored by the forward current-sensing circuitry 170. In the illustrated embodiment, when current is being drawn by the forward circuit, the rearward microcontroller 160 can transmit data to the forward microcontroller 150. More specifically, the rearward microcontroller toggles the gate of the rear main transistor 164. As shown in FIG. 3A, the toggling briefly and at least partially interrupts the current as sensed by the forward current-sensing circuitry. In the illustrated embodiment, the main transistors are metal-oxide-semiconductor transistors (MOSFET). However, it will be appreciated that alternate transistors (e.g., bi-polar junction transistors) may be utilized.

In any modulation scheme, logic supported by the microcontrollers allows decoding a modulated signal received from the other microcontroller. For instance, in the vaporizer embodiment, rearward-to-forward communication is used to relay a signal from an angle-position sensor 98 (i.e., temperature adjustment dial) located in the rearward section, to the forward section where the signal is processed and utilized by the forward microcontroller 150 to control the temperature of the heating element. The angle-position sensor 98 monitors the position of a user-adjustable temperature selection dial, but a similar circuit could be used for brightness control in a flashlight, or for any other means of user or environmental input applicable to the particular device. An output of the angle position sensor is received by the rearward microcontroller. This is encoded by the rearward microcontroller according to stored logic and the microcontroller operates the rearward main transistor to modulate the main circuit in accordance with the output of the angle sensor. By way of example only, the rearward microcontroller may provide a series of on-off modulations that correspond to the angular position and thereby selected temperature of the dial 98. For example, if the adjustable temperature range was 100° F., the rear microcontroller may modulate the main circuit once for each degree above the base temperature of the vaporizer. In this example, the forward microcontroller 150 would simply count the number of modulations and set the temperature of the heating element in accordance with the user selected temperature.

Figure 3B:
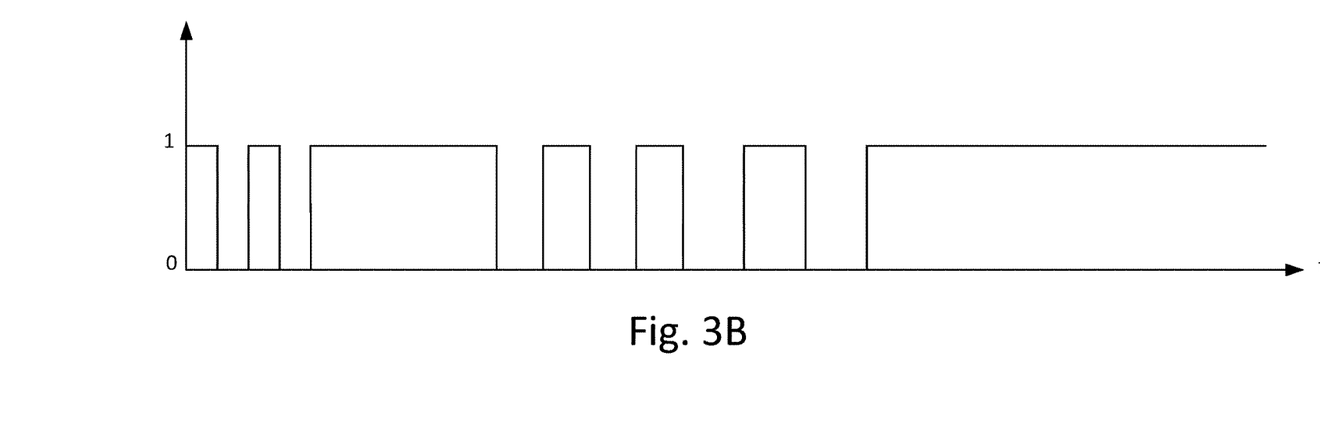

More complex modulation is possible and within the scope of the presented invention. As will be appreciated, the frequency and length of each modulation of the main circuit may varied. See, for example FIG. 3B. Accordingly, such variation provides the ability to encode considerable data. Further, the microcontrollers may include databases of modulation patterns and may match a received modulation of the main circuit by the other microcontroller to a pre-stored modulation patterns. Accordingly such modulation patterns may be indexed to any of a variety of functions.

The electrical system topology allows the forward and rearward control circuits to operate without interruption while those circuits are bypassed by or isolated from the main circuit. More specifically, the control circuits 70, 76 each include a capacitor bank 152, 162 that powers the microcontrollers and/or associated electronics during isolation. As will be appreciated, the capacitor banks must be recharged. In one arrangement, the control circuits operate to periodically recharge the capacitors. In this arrangement, switching is performed, for example, 10 times per second to ensure the capacitors are fully powered. In another arrangement, the microcontroller of the isolated control circuit is configured to monitor its own capacitor and signal to the other microcontroller when the charge falls below a predetermined threshold. That is, the isolated circuit requests power when needed by modulating the main circuit according to a predetermined modulation. Accordingly, when the other circuit identifies this modulation, the circuit switches to a passive mode to allow the requesting circuit access to the battery.

Referring again to FIGS. 2A and 2B, it should be noted if the load 100 (e.g., heater) is of sufficiently low impedance, the front bypass between terminals 155a and 155b as well as the forward main transistor 154 can be fully omitted. That is, if the secondary transistor 156 is conducting, meaning if the front control circuit is running the heater, the heater effectively behaves as a bypass in cases of low voltages. The rear can be powered by the main loop through the heater itself instead of the front bypass between terminals 155a and 155b, as the heater is essentially a bypass (with higher but inconsequential resistance).

The foregoing description has been presented for purposes of illustration and description. Furthermore, the description is not intended to limit the inventions and/or aspects of the inventions to the forms disclosed herein. Consequently, variations and modifications commensurate with the above teachings, and skill and knowledge of the relevant art, are within the scope of the presented inventions. The embodiments described hereinabove are further intended to explain best modes known of practicing the inventions and to enable others skilled in the art to utilize the inventions in such, or other embodiments and with various modifications required by the particular application(s) or use(s) of the presented inventions. It is intended that the appended claims be construed to include alternative embodiments to the extent permitted by the prior art.

What is claimed is:

1. An electrical system topology for use in a portable electronic device having a forward control circuit and a rearward control circuit connected in series via a battery and conductive housing that collectively define a main circuit loop, comprising:
   the forward control circuit including a forward controller for controlling the operation of a load, the forward control circuit further including:
      a forward bypass switch that in a first mode allows current from the battery to pass through the forward control circuit and in a second mode allows current from the battery to bypass the forward control circuit;
   the rearward control circuit including a rearward controller configured to provide an input to the forward control circuit for use in controlling the load, the rearward control circuit including:
      a rearward bypass switch that in the first mode allows current from the battery to bypass the rearward control circuit and in the second mode allows current from the battery to pass through the rearward control circuit;
   wherein the forward controller and the rearward controller operate in synchrony to switch the forward and rearward bypass switches to alter between the first and second modes.

2. The system of claim 1, wherein the forward and rearward controllers are further configured to:
   toggle a respective one of the bypass switches for modulating current flow of the main circuit loop.

3. The system of claim 2, wherein the modulation is performed in accordance with predetermined communication protocol stored by the controllers.

4. The system of claim 3, wherein each controller is further configured to:
   monitor modulation of the main circuit loop to receive data from the other of the controllers via the main circuit loop.

5. The system of claim 1, wherein the forward control circuit and the rearward control circuit further comprise, respectively:
   a forward capacitor, wherein in the second mode the capacitor discharges to provide power to the forward circuit and wherein in the first mode the forward capacitor receives power from the battery; and
   a rearward capacitor, wherein in the first mode the capacitor discharges to provide power to the rearward circuit and wherein in the second mode the rearward capacitor receives power from the battery.

6. The system of claim 1, wherein the bypass switches comprise transistors.

7. The system of claim 1, wherein the forward controller is configured to:
   monitor a change in a state of the main current loop caused by the rearward controller opening or closing the rearward bypass switch; and
   in response to the rearward bypass switch opening or closing, close or open the forward bypass switch.

8. The system of claim 7, wherein the rearward controller is operative to open and close the rearward bypass switch on a periodic basis.

9. The system of claim 1, wherein the portable electronic device comprises a vaporizer, wherein the load comprises a resistive heating element.

10. The system of claim 9, wherein the rearward controller is connected to an adjustable temperature dial, wherein the rearward controller provides a setting of the temperature dial to the forward controller.

11. The system of claim 1, wherein the load is disposed in series with the forward bypass switch.

12. A method for use in a portable electronic device, comprising
   connecting forward and rearward electronic control circuits in series with a first conductor and second conductor, wherein a battery is disposed in-line with one of the conductors and the control circuits and the conductors to define a main circuit loop through which current flows;
   operating forward and rearward controllers of the forward and rearward control circuits to open and close forward and rearward switches, respectively, to:
      in a first mode bypass the current around the rearward control circuit while passing the current through the forward control circuit; and
      in a second mode bypass the current around the forward control circuit while passing the current through the rearward control circuit, wherein in the first and second modes, the control circuit though which current is passing defines an active circuit and the other control circuit that current bypasses defines a passive circuit;
   operating the controller of the passive circuit using stored power;
   toggling one of the forward and rearward switches to modulate current flow through the main circuit loop to transfer data between the passive circuit and the active circuit.

13. The method of claim 12, wherein said toggling of said switches is performed pursuant to a stored communication protocol.

14. The method of claim 12, further comprising:
   monitoring, at the active control circuit, current in the main control to identify the modulation of the current flow initiated by the passive circuit.

15. The method of claim 14, further comprising:
   based on modulation of the current flow, altering operation of a load connected to the active circuit.

16. The method of claim 14, further comprising:
   based on modulation of the current flow, closing or opening one of said switches to change from one of said first and second modes of operation to the other of said first and second modes of operation.

17. The method of claim 12, further comprising:
   charging a capacitor of the active circuit.

* * * * *